United States Patent [19]

Goto et al.

[11] Patent Number: 5,154,851

[45] Date of Patent: Oct. 13, 1992

[54] LIQUID CRYSTAL COMPOUND HAVING LARGE OPTICAL ANISOTROPY VALUE

[75] Inventors: Yasuyuki Goto; Kisei Kitano, both of Chiba, Japan

[73] Assignee: Chisso Corporation, Osaka, Japan

[21] Appl. No.: 451,033

[22] Filed: Dec. 15, 1989

[30] Foreign Application Priority Data

Jan. 6, 1989 [JP] Japan ........................ 64-879

[51] Int. Cl.$^5$ .................... C09K 19/52; C09K 19/30
[52] U.S. Cl. .......................... 252/299.63; 252/299.01; 252/299.6; 252/299.66; 585/25
[58] Field of Search .......... 252/299.01, 299.6, 299.61, 252/299.63, 299.64, 299.65, 299.66, 299.67; 585/25

[56] References Cited

U.S. PATENT DOCUMENTS 3,925,482  12/1975  Jacques .................... 252/299.01
4,528,114   7/1985  Petrzilka .................. 252/299.6
4,705,905  11/1987  Takatsu et al. ............. 252/299.6

FOREIGN PATENT DOCUMENTS 0345013  12/1989  European Pat. Off. .
3734517   5/1989  Fed. Rep. of Germany .
3905932   9/1989  Fed. Rep. of Germany .
2145837   4/1985  United Kingdom .

Primary Examiner—Robert L. Stoll
Assistant Examiner—Shean C. Wu
Attorney, Agent, or Firm—Wenderoth, Lind & Ponack

[57] ABSTRACT

A liquid crystal compound is provided, having a large optical anisotropy Δn value and yet a low viscosity, and which can be added to a liquid crystal composition, without lowering the NI point of the composition and raising the viscosity thereof, while raising the Δn value thereof. The liquid crystal compound is a 4-substituted-4'-(1-alkynyl)tolan expressed by the formula

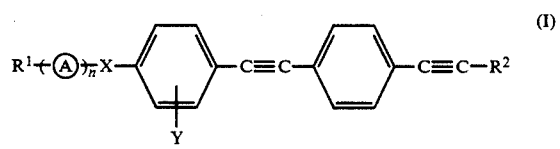

(I)

wherein $R^1$ and $R^2$ each is 1-8C alkyl and one $CH_2$ group or two non-adjacent $CH_2$ groups present therein may be replaced by any one of O, —CO—, —CO—O—, —O—CO— or —$CH_2$=$CH_2$—; —(A)— is unsubstituted 1,4-phenylene, 1,4-phenylene having one or two F, Cl or Br atoms or CN groups, 1,4-cyclohexylene, pyrimidine-2,5-diyl or 1,3-dioxane-2,5-diyl; X is —COO—, —OCO—, —$CH_2$—$CH_2$—, —$OCH_2$—, —$CH_2O$—, —CH=CH— or a single bond; n is 0 or 1 and when n is 0, X is a single bond; and Y is H or F.

7 Claims, 2 Drawing Sheets

RELATIONSHIP BETWEEN RATIO OF ELASTIC CONSTANTS AND $\gamma$-CHARACTERISTICS (180° TWIST, 230° TWIST)

LIQUID CRYSTAL COMPOUND HAVING LARGE OPTICAL ANISOTROPY VALUE

BACKGROUND OF THE INVENTION

1. Field of the Invention

This invention relates to a substituted benzene derivative used as a component of a liquid crystal and a liquid crystal composition containing the same, having superior characteristics.

2. Description of the Related Art

Display devices having applied liquid crystals are those utilizing an electrooptical effect based on the dielectric anisotropy and electroconductive anisotropy of liquid crystal substances. Liquid crystal display modes include various ones such as dynamic scattering mode, twist nematic mode, supertwist nematic mode, phase transition mode, DAP mode, guest-host mode, etc. Properties required for liquid crystal substances used for liquid crystal displays vary depending on the respective liquid crystal display modes, but a broad mesomorphic range, stability to moisture, air, light, heat, electricity, etc. are required for any of the display modes commonly employed. Further, it is also required that the response of display elements is rapid and the devices can be driven at a voltage as low as possible when the substances are used for liquid crystal display devices. At present, however, there is no single compound which satisfies all of such requirements, but there have been practically used liquid crystal mixtures obtained by mixing several kinds of liquid crystal compounds or mixing them with compounds similar to liquid crystals compounds.

Recently, in order to provide a liquid crystal display element having a good pictorial quality even in a multiplex number of 100 or more, it has been proposed to change the cell structure having the twist angle of the helical structure of liquid crystal molecule, combined with the polarizing plate to a new mode (e.g. Japanese patent application laid-open Nos. Sho 60-50511/1985, Sho 60-50454/1985, etc.)

The object of the present invention is to provide a liquid crystal compound suitable for a liquid crystal composition for liquid crystal display elements, particularly suitable to the above new mode structure.

The liquid crystal elements of a cell structure having an enlarged twist angle of liquid crystal molecules exhibits an entirely different effect in the values of physical properties obtained by choice of liquid crystal materials, from those in the case of conventional 90° twist. Characteristics of liquid crystal display elements having an enlarged twist angle are shown in FIG. 1, as compared with those in the case of conventional 90° twist. FIGS. 1a and 1b each show the viewing angle-dependency of voltage-transmittance characteristics in the cases of 90° twist and 180° twist. As seen from FIGS. 1a and 1b, the element having a 180° twist structure is steep in the decay characteristics ($\gamma$ characteristics) of the transmittance by impressed voltage; thus it is evidently improved in the characteristics as compared with the case of conventional 90° twist. This tendency is notable with an increase in the twist angle. As described above, since an element structure having an enlarged twist angle affords a steepness to the decay characteristics by impression of voltage, the difference between the transmittance by impression of voltage and that by non-impression of voltage at the time of multiplex drive becomes large, thus a higher multiplex drive than the conventional one becomes possible.

However, as to the relationship between the $\gamma$ characteristics in the case of 90° twist and the $\gamma$ characteristics in the case of about 200° twist, the same tendency is not exhibited depending on liquid crystal materials, but there has appeared a phenomenon which does not apply to the following report that, in general, the $\gamma$ characteristics in the case of 90° twist are better when the ratio of the elastic constants ($K_{33}/K_{11}$) is smaller (Euro Display 84 "Liquid crystal properties in relation to multiplexing requirements", Gunter Baur). This is presumed to be related to the change of the elastic constant and other factors due to the enlargement of twist angle, but it has not yet been theoretically elucidated. FIG. 2 shows the relationship between the ratio of the elastic constants and $\gamma$ characteristics in the case of 180° twist and that in the case of 230° twist, with two compounds i.e. a pyrimidine compound and a PCH (phenylcyclohexane) compound, respectively. As seen from this figure, the pyrimidine compound having a smaller elastic constant exhibits inferior results of $\gamma$ characteristics to those of the PCH compound. As described above, in the case of about 200° twist, a conventional thought is not applied thereto; hence it is necessary to choose liquid crystal materials from an entirely different way of thinking from that in the case of 90° twist cell structure. As described above, by enlarging the twist angle or selecting liquid crystal materials, a liquid crystal material having superior $\gamma$ characteristics is obtained. However, as shown in FIG. 3, by improving $\gamma$ characteristics, it has been found that the better the $\gamma$ characteristics of liquid crystal materials, the smaller the response rate. When the response properties are taken into consideration, choice of only materials having superior $\gamma$ characteristics is not always sufficient, but in order to obtain a liquid crystal display element having superior response properties, while retaining superior $\gamma$ characteristics to a certain extent, a method of reducing the thickness of the liquid crystal layer can be considered.

Thus, when the thickness of the liquid crystal layer is reduced in order to improve response properties, the $\Delta n$ of the material should be varied according to the thickness of the liquid crystal layer. For example, in the case of 200° twist, the product of the $\Delta n$ of liquid crystal material by the thickness d of the liquid crystal phase ($\Delta n \cdot d$) is best in the vicinity of 0.96 $\mu m$; hence when the liquid crystal layer has a thickness d of 7 $\mu m$, the $\Delta n$ of the material should be adjusted to 0.137. Further, in order to make the thickness d of the liquid crystal layer 5 $\mu m$ for improving the response rate, it is necessary to increase the $\Delta n$ value greatly up to 0.192. As described above, in order to correspond to the reduction in the thickness of the liquid crystal layer, the $\Delta n$ of the material should be increased, but this case is accompanied with a problem of viscosity. As to the relationship between the $\Delta n$ and the viscosity of liquid crystal materials so far reported, there has been clarified a tendency that the viscosity increases with increase in the $\Delta n$. In such a situation, among conventional materials, those having a large $\Delta n$ value and yet a low viscosity have been very few.

As examples of compounds having a large optical anisotropy ($\Delta n$) value, used as a component of liquid crystal materials, compounds expressed by the following formulas (1)–(6) have been disclosed in the following references, respectively:

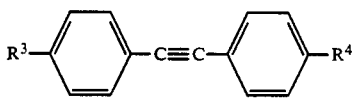 (1)

wherein R³ and R⁴ each represent an alkyl group or an alkoxy group.

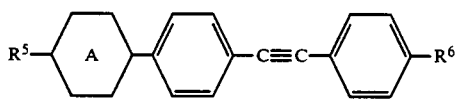 (2)

wherein

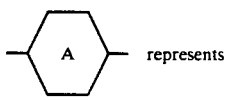 represents

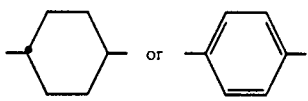 or and R⁵ and R⁶ each represent a linear alkyl group.

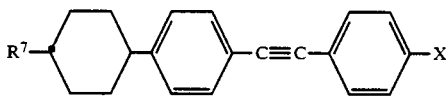 (3)

wherein R⁷ represents a linear alkyl group and X represents a halogen atom.

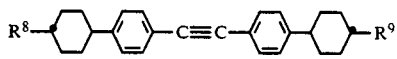 (4)

wherein R⁸ and R⁹ each represent a linear alkyl group.

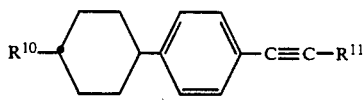 (5)

wherein R¹⁰ and R¹¹ each represent a linear alkyl group.

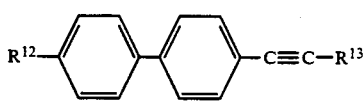 (6)

wherein R¹² and R¹³ each represent a linear alkyl group.

(1) French patent application laid-open No. 2,141,438 (corresponding U.S. Pat. No. 3,925,482)
(2) Japanese patent application laid-open No. Sho 60-15427/1985 (corresponding U.S. Pat. No. 4,705,905)
(3) Japanese patent application laid-open No. Sho 61-260031/1986
(4) Japanese patent application laid-open No. Sho 60-204731 (1985) (corresponding U.S. Pat. No. 4,705,905)
(5) Japanese patent application laid-open No. Sho 58-110527 (1983) (corresponding to U.S. Pat. No. 4,528,114)
(6) Ditto These tolan derivatives are said to have a large Δn value and a relatively low viscosity, but recently, those far exceeding the characteristics of these compounds are required.

SUMMARY OF THE INVENTION

The present invention resides in a 4-substituted-4'-(1-alkynyl)tolan expressed by the formula (I)

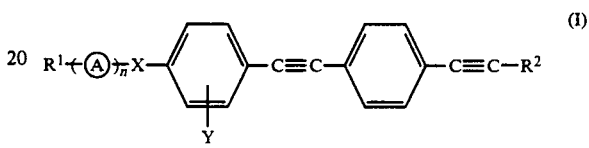 (I)

wherein R¹ and R² each represent an alkyl group of 1 to 8 carbon atoms and one CH₂ group or two CH₂ groups not adjacent therein may be replaced by any one of O atom, —CO— group, —CO—O— group, —O—CO— group or —CH=CH— group; —(A)— represents unsubstituted 1,4-phenylene, 1,4-phenylene having one or two F, Cl or Br atoms or CN groups as substituents, 1,4-cyclohexylene, pyrimidine-2,5-diyl or 1,3-dioxane-2,5-diyl; X represents —COO—, —OCO—, —CH₂CH₂—, —OCH₂—, —CH₂O—, —CH=CH— or a single bond; n represents 0 or 1 and when n represents 0, X represents a single bond; and Y represents H or F, and a liquid crystal composition containing the compound of the formula (I).

Figure 1A:
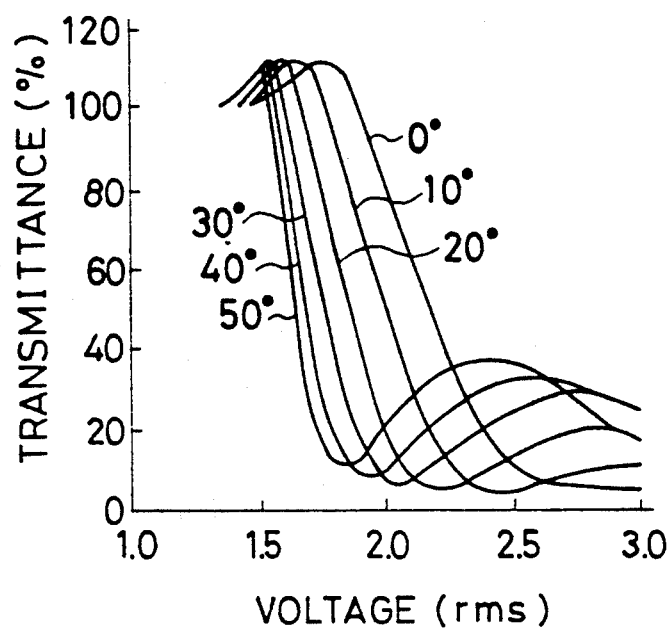
FIG. 1a shows a chart illustrating the angle-dependency of an element exhibiting a twist angle of 90°.
Figure 1B:
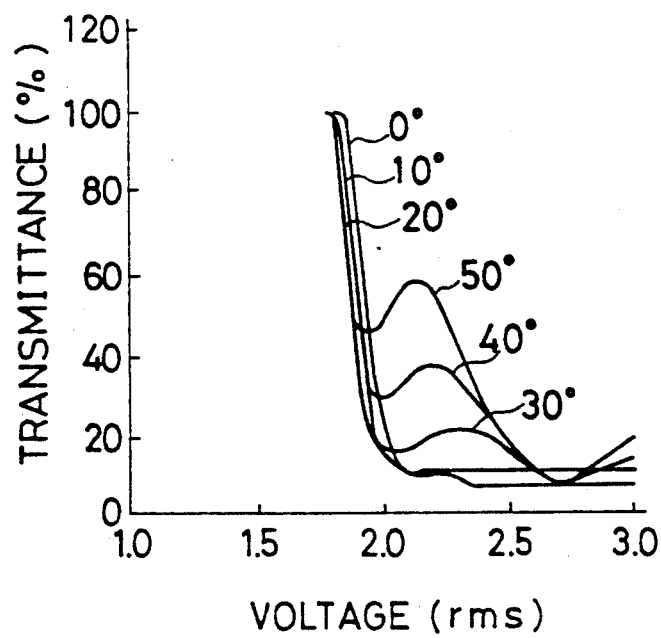
FIG. 1b shows a chart illustrating the angle-dependency of the voltage-transmittance characteristics of an element exhibiting a twist angle of 180°.
Figure 2:
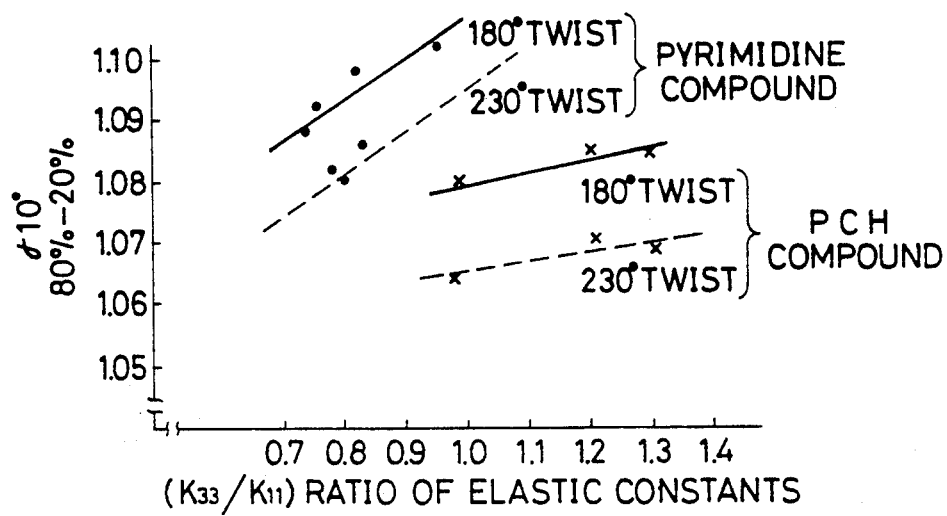
FIG. 2 shows a chart illustrating the respective relationships between the ratio of elastic constants and γ characteristics of elements of 180° twist angle and 230° twist angle.
Figure 3:
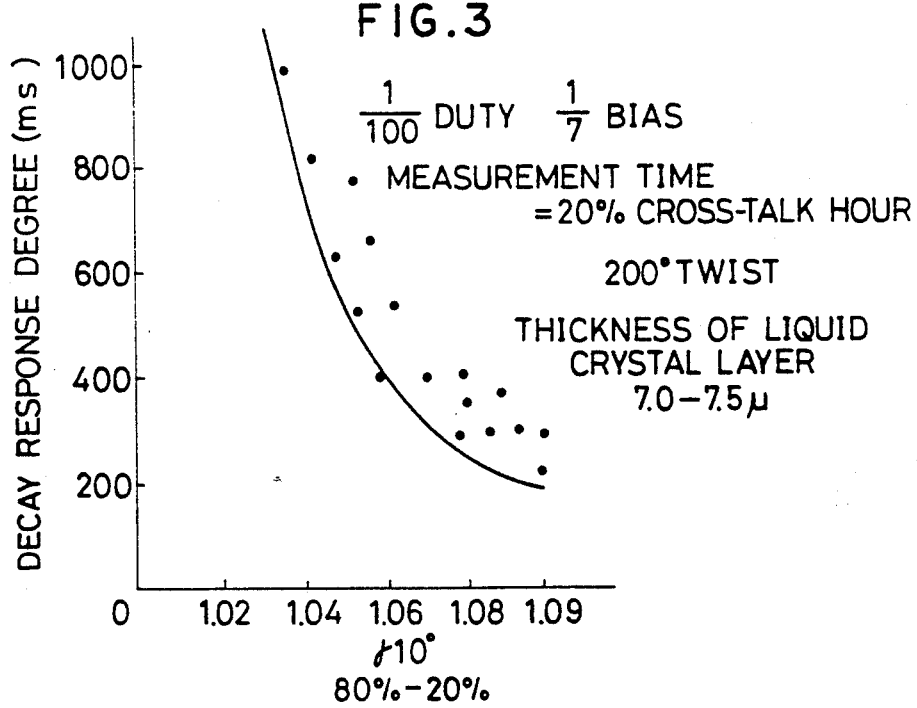
FIG. 3 shows a chart illustrating the relationship between the γ characteristics and the decay response rate of a conventional liquid crystal material.

Herein, $\gamma^{10°}_{80\%-20\%}$ refers to γ characteristics in terms of a ratio of a voltage at a transmittance of 80% to that at a transmittance of 20° C. at an angle of 10° against the normal.

DETAILED DESCRIPTION OF PREFERRED EMBODIMENTS

The compound of the formula (I) includes compounds of the following formulas Ia to Ih as preferred compounds:

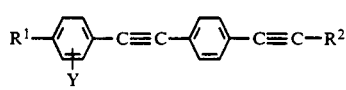 Ia

-continued

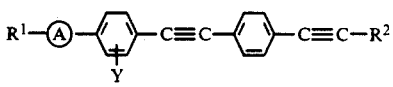 Ib

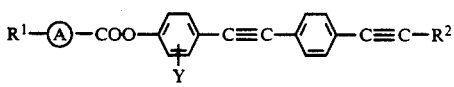 Ic

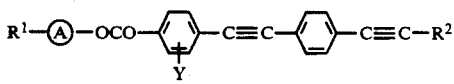 Id

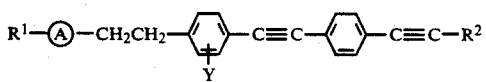 Ie

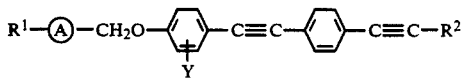 If

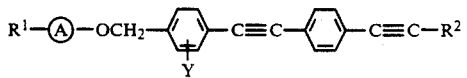 Ig

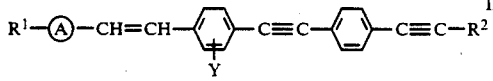 Ih

In these formulas, $R^1$, $R^2$, —Ⓐ— and Y are as defined above.

Among the compounds of the above formulas, those of the formulas Ia, Ib, Ic and Ie are preferred. Further, among these compounds, those of the formulas Iba, Ibb, Ica, Icb and Iea in the following formulas are particularly preferred.

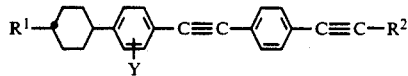 Iba

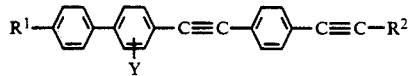 Ibb

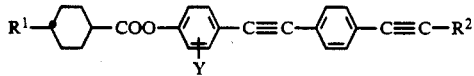 Ica

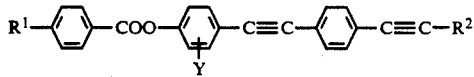 Icb

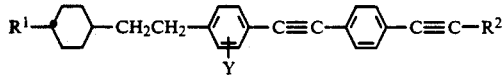 Iea

In the compounds of the above formulas, as to alkyl groups $R^1$ and $R^2$, one $CH_2$ group or two —$CH_2$ groups not adjacent to each other, present therein may be replaced by any one of O atom, —CO group, —CO—O— group, —O—CO— group or CH=CH— group, and the alkyl groups may be branched chain alkyl groups.

$R^1$ and $R^2$ are each preferably linear and have 1 to 8 carbon atoms. Further, $R^2$ is particularly preferred to be a linear, normal alkyl group, the —$CH_2$ groups of which are not replaced by O atom.

Compounds of the formula (I) having branched side chain groups $R^1$ and $R^2$ have an improved solubility in conventional liquid crystal base materials; hence they are important in some cases, and when they are optically active, they are important as a chiral dopant. The branched chain groups of such kind generally have at least one chain branch.

Among the compounds of the present invention, for example, two-ring compounds expressed by the formula Ia have an optical anisotropy Δn value as very large as about 0.35, and further a viscosity at 20° C. as low as about 22 cp, and hence have well-balanced characteristics for liquid crystal materials. Hence it is possible to increase the Δn value of the liquid crystal composition containing the compound of the present invention without raising the viscosity of the composition.

Next, an embodiment of the production process of the compound of the present invention will be illustrated by the following equation:

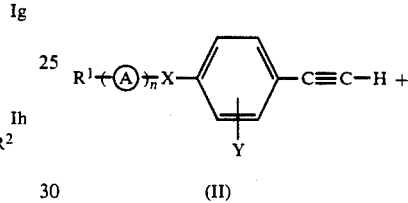

(II)

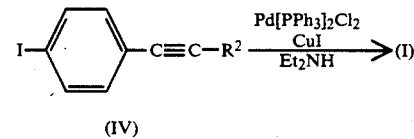

(IV)

In the above equation, $R^1$, $R^2$, —Ⓐ—, n, X and Y are as defined above.

Namely, a substituted-phenylacetylene (II) obtained according to a known method (Chem. Ber., 89, 1755 (1956) is reacted with a 4-(1-alkynyl)iodobenzene (IV) in the presence of a palladium catalyst such as bistriphenylphosphinepalladium dichloride and copper iodide in a solvent of diethylamine according to a method in the literature (Tetrahedron Letters No. 50, pp 4467–70 (1975), followed by purification according to a conventional method, to obtain the objective compound of the formula (I).

The liquid crystal composition of the present invention consists of 2 to 25 kinds, preferably 3 to 15 kinds of components containing at least one compound expressed by the formula (I). Components other than the compound of the formula (I) are preferred to be nematic liquid crystal substances. Examples of known compounds among such substances are particularly azoxybenzene compounds, benzylideneaniline compounds, biphenyl compounds, terphenyl compounds, phenyl or cyclohexyl benzoate compounds, phenyl or cyclohexyl cyclohexanecarboxylate compounds, phenylcyclohexane compounds, cyclohexylbiphenyl compounds, cyclohexylcyclohexane compounds, cyclohexylnaphthalene compounds, 1,4-biscyclohexylbenzene compounds, 4,4'-biscyclohexylbiphenyl compounds, phenylpyrimidine compounds, cyclohexylpyrimidine compounds, phenylpyridazine compounds or cyclohexylpyridazine compounds, N-oxide compounds thereof, phenyldioxane compounds, cyclohexyldioxane compounds, phenyl-1,3-dithian compounds, cyclohexyl-1,3-dithian compounds, 1,2-diphenylethane compounds, 1-phenyl-2-cyclohexyl-ethane compounds, 1,2-dicyclohexylethane compounds, and in some cases, halogenated stilbene compounds, benzyl phenyl ether compounds, tolan compounds, substituted cinnamic acid compounds, etc.

Among these compounds, important compounds may be expressed by the formula

R'—L—G—E—R''  (I')

wherein L and E each represent carbocyclic or heterocyclic compounds belonging to groups consisting of 1,4-di-substituted benzenes, cyclohexane ring 4,4'-di-substituted biphenyls, phenylcyclohexanes, cyclohexylcyclohexanes, phenylbicyclohexanes, 2,5-di-substituted naphthalenes, dihydronaphthalenes, tetrahydronaphthalenes, quinazoline and tetrahydroquinazoline; G represents —CH=CH—, —N(O)=N—, —CH=CY—, —CH=N(O)—, —C≡C—, —CH$_2$—CH$_2$—, —CO—O—, —CH$_2$O—, —CO—S—, —CH$_2$S—, —CH=N—, —COO—Phe—COO— or C—C single bond, Y representing a halogen (preferably chlorine) atom or —CN; and R' and R'' each represent alkyl, alkoxy, alkanoyloxy, alkoxycarbonyl or alkoxycarbonyloxy each of up to 18 carbon atoms, preferably up to 8 carbon atoms, or either one of R' and R'' represents CN, NC, NO$_2$, CF$_3$, F, Cl, or Br.

In most of these compounds, R' and R'' are different from each other, and either one of these groups represents, in most cases, an alkyl group or an alkoxy group. In these compounds, conventional substituents for these groups are usable. Most of the substances expressed by the formula (I') and mixtures thereof are commercially available. All of these substances can be obtained according to known methods disclosed in literatures.

The composition of the present invention contains at least one compound of the formula (I) in a content of about 0.1 to 40% by weight based on the composition. A liquid crystal composition of the present invention containing at least one compound of the formula (I) in a quantity of 10 to 30% by weight is particularly preferred.

The composition of the present invention itself is prepared in a conventional manner. In general, the constituting components are dissolved in one another, preferably at an elevated temperature.

Further, a superior liquid crystal element is provided using the compound of the present invention. Such an element is characterized in that a nematic liquid crystal having a positive dielectric anisotropy value and having a rotatory polarization substance added thereto is sealed between a pair of upper and lower electrode substrates opposed to each other; liquid crystal molecules form a 160°–270°-twisted, helical structure in the thickness direction thereof; thereof; the polarization axis of polarizing plates provided for placing the helical structure therebetween deviates within a range of 20° to 70° against the direction of liquid crystal molecule arrangement in the electrode substrates; the product of the thickness of the liquid crystal layer (d) by the optical anisotropy value of the liquid crystal layer (Δn), that is, Δn×d, is in the range of 0.7 to 1.2 μm; and a liquid crystal composition containing 0.1 to 40% by weight based on the composition, of at least one tolan compound of the present invention, is contained in the liquid crystal element.

The present invention will be described in more detail by way of Examples, but it should not be construed to be limited thereto. In the Examples, CI point represents crystal-isotropic liquid phase transition point and NI point represents nematic phase-isotropic liquid phase transition point. All temperatures refer to ° C.

EXAMPLE 1

Preparation of 4-propyl-4'-(1-propynyl)tolan

4-Propylphenylacetylene (7.21 g, 0.05 mol) and 4-(1-propynyl)iodobenzene (12.1 g, 0.05 mol) were dissolved in diethylamine (30 cc), and then copper iodide (0.29 g, 1.5 mmol) and dichlorobistriphenylphosphinepalladium dichloride (0.53 g, 0.75 mmol) were added. The resulted mixture was reacted with stirring in nitrogen gas current at about 20° C. for 8 hours. After completion of the reaction, water (100 ml) was added to the resulting reaction mixture. The resulting deposited mass was extracted with toluene (50 ml). The resulting toluene solution was washed with dilute hydrochloric acid, followed by water until the washing water became neutral. The resulting material was dried over anhydrous sodium sulfate. Toluene was distilled off from the toluene solution. The residue was then dissolved in a mixed solvent of n-hexane/methylene chloride (1 vol./1 vol.). The solution was subjected to column chromatography using silica gel as a fixed phase, and using the above mixed solvent as an eluent. Fractions showing a single spot were collected by TLC and the mixed solvent was distilled. The residue after distillation was recrystallized from ethyl alcohol (20 ml) to obtain the objective 4-propyl-4'-(1-propynyl)tolan (compound No. 1) (6.7 g). This compound exhibited liquid crystal phases (CI point: 87.7° C., NI point: 85.1° C.).

The following compounds are prepared in the same manner as above:

Compound No. 2: 4-ethyl-4'-(1-propynyl)tolan
No. 3: 4-ethyl-4'-(1-butynyl)tolan (CI point: 83.1° C.)
No. 4: 4-ethyl-4'-(1-pentynyl)tolan (CI point: 89.8° C.)
No. 5: 4-ethyl-4'-(1-hexynyl)tolan
No. 6: 4-ethyl-4'-(1-heptynyl)tolan
No. 7: 4-ethyl-4'-(1-octynyl)tolan
No. 8: 4-ethyl-4'-(1-nonynyl)tolan
No. 9: 4-ethyl-4'-(1-decynyl)tolan
No. 10: 4-propyl-4'-(1-butynyl)tolan (CI point: 100.1° C., NI point: 48.7° C.)
No. 11: 4-propyl-4'-(1-pentynyl)tolan (CI point: 78.0° C., NI point: 54.0° C.)
No. 12: 4-propyl-4'-(1-hexynyl)tolan
No. 13: 4-propyl-4'-(1-heptynyl)tolan
No. 14: 4-propyl-4'-(1-octynyl)tolan
No. 15: 4-propyl-4'-(1-nonynyl)tolan
No. 16: 4-propyl-4'-(1-decynyl)tolan
No. 17: 4-butyl-4'-(1-propynyl)tolan (CI point: b 81.0° C., NI point: 59.6° C.)
No. 18: 4-butyl-4'-(1-butynyl)tolan (CI point: 87.6° C., NI point: 76.8° C.)
No. 19: 4-butyl-4'-(1-pentynyl)tolan (CI point: 100.9° C., NI point: 65.0° C.)
No. 20: 4-butyl-4'-(1-hexynyl)tolan (CI point: 84.3° C.)
No. 21: 4-butyl-4'-(1-heptynyl)tolan
No. 22: 4-butyl-4'-(1-octynyl)tolan
No. 23: 4-butyl-4'-(1-nonynyl)tolan
No. 24: 4-butyl-4'-(1-decynyl)tolan
No. 25: 4-pentyl-4'-(1-propynyl)tolan No. 26: 4-pentyl-4'-(1-butynyl)tolan (CI point: 80.8° C., NI point: 46.1° C.)
No. 27: 4-pentyl-4'-(1-pentynyl)tolan (CI point: 76.2° C., NI point: 50.3° C.)
No. 28: 4-pentyl-4'-(1-hexynyl)tolan (CI point: 75.4° C.)
No. 29: 4-pentyl-4'-(1-heptynyl)tolan
No. 30: 4-pentyl-4'-(1-octynyl)tolan
No. 31: 4-pentyl-4'-(1-nonynyl)tolan
No. 32: 4-pentyl-4'-(1-decynyl)tolan
No. 33: 4-hexyl-4'-(1-propynyl)tolan
No. 34: 4-hexyl-4'-(1-butynyl)tolan
No. 35: 4-hexyl-4'-(1-pentynyl)tolan
No. 36: 4-hexyl-4'-(1-hexynyl)tolan
No. 37: 4-hexyl-4'-(1-heptynyl)tolan
No. 38: 4-hexyl-4'-(1-octynyl)tolan
No. 39: 4-hexyl-4'-(1-nonynyl)tolan
No. 40: 4-hexyl-4'-(1-decynyl)tolan
No. 41: 4-heptyl-4'-(1-propynyl)tolan
No. 42: 4-heptyl-4'-(1-butynyl)tolan
No. 43: 4-heptyl-4'-(1-pentynyl)tolan
No. 44: 4-heptyl-4'-(1-hexynyl)tolan
No. 45: 4-heptyl-4'-(1-heptynyl)tolan
No. 46: 4-heptyl-4'-(1-octynyl)tolan
No. 48: 4-heptyl-4'-(1-decynyl)tolan
No. 49: 4-octyl-4'-(1-propynyl)tolan
No. 50: 4-octyl-4'-(1-butynyl)tolan
No. 51: 4-octyl-4'-(1-pentynyl)tolan
No. 52: 4-octyl-4'-(1-hexynyl)tolan
No. 53: 4-octyl-4'-(1-heptynyl)tolan
No. 54: 4-octyl-4'-(1-octynyl)tolan
No. 55: 4-octyl-4'-(1-nonynyl)tolan
No. 56: 4-octyl-4'-(1-decynyl)tolan

EXAMPLE 2

Preparation of 4-(trans-4-propylcyclohexyl)-4'-(1-propynyl)tolan

Trans-4-propylcyclohexylphenylacetylene (2.3 g, 0.01 mol) and 4-(1-propynyl)iodobenzene (2.4 g, 0.01 mol) were dissolved in diethylamine (20 ml), and then copper iodide (0.11 g, 0.15 mmol) and dichlorobistriphenylphosphinepalladium dichloride (0.21 g, 0.3 mmol) were added. The resulting mixture was subjected to reaction and purification operation in the same manner as in Example 1 to obtain the objective 4-(trans-4-propylcyclohexyl)-4'-(1-propyl)tolan (compound No. 57) (1.8 g). (CS point: 118.9° C., SN point: 127.4° C., NI point: 245.1° C.)

The following compounds are prepared in the same manner as above:
Compound No. 58: 4-(trans-4-ethylcyclohexyl)-4'-(1-propynyl)tolan
No. 59: 4-(trans-4-ethylcyclohexyl)-4'-(1-butynyl)tolan
No. 60: 4-(trans-4-ethylcyclohexyl)-4'-(pentynyl)tolan
No. 61: 4-(trans-4-ethylcyclohexyl)-4'-(hexynyl)tolan
No. 62: 4-(trans-4-ethylcyclohexyl)-4'-(heptynyl)tolan
No. 63: 4-(trans-4-ethylcyclohexyl)-4'-(1-octynyl)tolan
No. 64: 4-(trans-4-ethylcyclohexyl)-4'-(1-nonynyl)tolan
No. 65: 4-(trans-4-ethylcyclohexyl)-4'-(1-decynyl)tolan
No. 66: 4-(trans-4-propylcyclohexyl)-4'-(1-butynyl)tolan
No. 67: 4-(trans-4-propylcyclohexyl)-4'-(1-pentynyl)tolan
No. 68: 4-(trans-4-propylcyclohexyl)-4'-(1-hexynyl)tolan
No. 69: 4-(trans-4-propylcyclohexyl)-4'-(1-heptynyl)tolan
No. 70: 4-(trans-4-propylcyclohexyl)-4'-(1-octynyl)tolan
No. 71: 4-(trans-4-propylcyclohexyl)-4'-(1-nonynyl)tolan
No. 72: 4-(trans-4-propylcyclohexyl)-4'-(1-decynyl)tolan
No. 73: 4-(trans-4-butylcyclohexyl)-4'-(1-propynyl)tolan
No. 74: 4-(trans-4-butylcyclohexyl)-4'-(1-butynyl)tolan
No. 75: 4-(trans-4-butylcyclohexyl)-4'-(1-pentynyl)tolan
No. 76: 4-(trans-4-butylcyclohexyl)-4'-(1-hexynyl)tolan
No. 77: 4-(trans-4-butylcyclohexyl)-4'-(1-heptynyl)tolan
No. 78: 4-(trans-4-butylcyclohexyl)-4'-(1-octynyl)tolan
No. 79: 4-(trans-4-butylcyclohexyl)-4'-(1-nonynyl)tolan
No. 80: 4-(trans-4-butylcyclohexyl)-4'(decynyl)tolan
No. 81: 4-(trans-4-pentylcyclohexyl)-4'-(propynyl)tolan
No. 82: 4-(trans-4-pentylcyclohexyl)-4'-(butynyl)tolan
No. 83: 4-(trans-4-pentylcyclohexyl)-4'-(1-pentynyl)tolan
No. 84: 4-(trans-4-pentylcyclohexyl)-4'-(1-hexynyl)tolan
No. 85: 4-(trans-4-pentylcyclohexyl)-4'-(1-heptynyl)tolan
No. 86: 4-(trans-4-pentylcyclohexyl)-4'- < -(1-octynyl)tolan
No. 87: 4-(trans-4-pentylcyclohexyl)-4'-(1-nonynyl)tolan
No. 88: 4-(trans-4-pentylcyclohexyl)-4'-(1-decynyl)tolan
No. 89: 4-(trans-4-hexylcyclohexyl)-4'-(1-propynyl)tolan
No. 90: 4-(trans-4-hexylcyclohexyl)-4'-(1-butynyl)tolan
No. 91: 4-(trans-4-hexylcyclohexyl)-4'-(1-pentynyl)tolan
No. 92: 4-(trans-4-hexylcyclohexyl)-4'-(1-hexynyl)tolan
No. 93: 4-(trans-4-hexylcyclohexyl)-4'-(1-heptynyl)tolan
No. 94: 4-(trans-4-hexylcyclohexyl)-4'-(1-octynyl)tolan
No. 95: 4-(trans-4-hexylcyclohexyl)-4'-(1-nonylyl)tolan
No. 96: 4-(trans-4-hexylcyclohexyl)-4'-(1-decynyl)tolan
No. 97: 4-(trans-4-heptylcyclohexyl)-4'-(1-propynyl)tolan
No. 98: 4-(trans-4-heptylcyclohexyl)-4'-(1-butynyl)tolan
No. 99: 4-(trans-4-heptylcyclohexyl)-4'-(1-pentynyl)tolan
No. 100: 4-(trans-4-heptylcyclohexyl)-4'-(1-hexynyl)tolan
No. 101: 4-(trans-4-heptylcyclohexyl)-4'-(1-heptynyl)tolan
No. 102: 4-(trans-4-heptylcyclohexyl)-4'-(1-octynyl)tolan
No. 103: 4-(trans-4-heptylcyclohexyl)-4'-(1-nonynyl)tolan
No. 104: 4-(trans-4-heptylcyclohexyl)-4'-(1-decynyl)tolan
No. 105: 4-(trans-4-octylcyclohexyl)-4'-(1-propynyl)tolan
No. 106: 4-(trans-4-octylcyclohexyl)-4'-(1-butynyl)tolan
No. 107: 4-(trans-4-octylcyclohexyl)-4'-(1-pentynyl)tolan
No. 108: 4-(trans-4-octylcyclohexyl)-4'-(1-hexynyl)tolan No. 109: 4-(trans-4-octylcyclohexyl)-4'-(1-heptynyl)tolan
No. 110: 4-(trans-4-octylcyclohexyl)-4'-(1-octynyl)tolan
No. 111: 4-(trans-4-octylcyclohexyl)-4'-(1-nonylyl)tolan
No. 112: 4-(trans-4-octylcyclohexyl)-4'-(1-decynyl)tolan
No. 113: 2-fluoro-4-(trans-4-propylcyclohexyl)-4'-(1-propynyl)tolan
No. 114: 2-fluoro-4-(trans-4-propylcyclohexyl)-4'-(1-butynyl)tolan
No. 115: 2-fluoro-4-(trans-4-propylcyclohexyl)-4'-(1-pentynyl)tolan
No. 116: 2-fluoro-4-(trans-4-butylcyclohexyl)-4'-(1-propynyl)tolan
No. 117: 2-fluoro-4-(trans-4-butylcyclohexyl)-4'-(1-butynyl)tolan
No. 118: 2-fluoro-4-(trans-4-butylcyclohexyl)-4'-(1-pentynyl)tolan
No. 119: 2-fluoro-4-(trans-4-pentylcyclohexyl)-4'-(1-propynyl)tolan
No. 120: 2-fluoro-4-(trans-4-pentylcyclohexyl)-4'-(1-butynyl)tolan
No. 121: 2-fluoro-4-(trans-4-pentylcyclohexyl)-4'-(1-pentynyl)tolan
No. 121-2: 2-fluoro-4-(trans-4-pentylcyclohexyl)-4'-(1-hexynyl)tolan (CS point: 51.3° C., SN point: 102.2° C., and NI point: 201.3° C.)

EXAMPLE 3

Preparation of 4-[2-(trans-4-propylcyclohexyl)ethyl]-4'-(1-propynyl)tolan

4-[2-(Trans-4-propylcyclohexyl)ethyl]phenylacetylene (2.54 g, 0.01 mol) and 4-(1-propynyl)iodobenzene (2.4 g, 0.01 mol) were dissolved in diethylamine (20 ml), and then copper iodide (0.11 g, 0.15 mmol) and dichlorobistriphenylphosphinepalladium dichloride (0.21 g, 0.3 mmol) were added. The resulting mixture was subjected to reaction and purification operations in the same manner as in Example 1, to obtain the objective 4-[2-(trans-4-propylcyclohexyl)ethyl]-4'-(1-propynyl)tolan (compound No. 122) (1.6 g).

The following compounds are prepared in the same manner as above:
No. 123: 4-[2-(trans-4-ethylcyclohexyl)ethyl]-4'-(1-propynyl)tolan
No. 124: 4-[2-(trans-4-ethylcyclohexyl)ethyl]-4'-(1-butynyl)tolan
No. 125: 4-[2-(trans-4-ethylcyclohexyl)ethyl]-4'-(1-pentynyl)tolan
No. 126: 4-[2-(trans-4-ethylcyclohexyl)ethyl]-4'-(1-hexynyl)tolan
No. 127: 4-[2-(trans-4-ethylcyclohexyl)ethyl]-4'-(1-heptynyl)tolan
No. 128: 4-[2-(trans-4-ethylcyclohexyl)ethyl]-4'-(1-octynyl)tolan
No. 129: 4-[2-(trans-4-ethylcyclohexyl)ethyl]-4'-(1-nonynyl)tolan
No. 130: 4-[2-(trans-4-ethylcyclohexyl)ethyl]-4'-(1-decynyl)tolan
No. 131: 4-[2-(trans-4-propylcyclohexyl)ethyl]-4'-(1-butynyl)tolan
No. 132: 4-[2-(trans-4-propylcyclohexyl)ethyl]-4'-(1-pentynyl)tolan
No. 133: 4-[2-(trans-4-propylcyclohexyl)ethyl]-4'-(1-hexynyl)tolan
No. 134: 4-[2-(trans-4-propylcyclohexyl)ethyl]-4'-(1-heptynyl)tolan
No. 135: 4-[2-(trans-4-propylcyclohexyl)ethyl]-4'-(1-octynyl)tolan
No. 136: 4-[2-(trans-4-propylcyclohexyl)ethyl]-4'-(1-nonynyl)tolan
No. 137: 4-[2-(trans-4-propylcyclohexyl)ethyl]-4'-(1-decynyl)tolan
No. 138: 4-[2-(trans-4-butylcyclohexyl)ethyl]-4'-(1-propynyl)tolan
No. 139: 4-[2-(trans-4-butylcyclohexyl)ethyl]-4'-(1-butynyl)tolan
No. 140: 4-[2-(trans-4-butylcyclohexyl)ethyl]-4'-(1-pentynyl)tolan
No. 141: 4-[2-(trans-4-butylcyclohexyl)ethyl]-4'-(1-heptynyl)tolan
No. 142: 4-[2-(trans-4-butylcyclohexyl)ethyl]-4'-(1-octynyl)tolan
No. 143: 4-[2-(trans-4-butylcyclohexyl)ethyl]-4'-(1-nonynyl)tolan
No. 144: 4-[2-(trans-4-butylcyclohexyl)ethyl]-4'-(1-decynyl)tolan
No. 145: 4-[2-(trans-4-pentylcyclohexyl)ethyl]-4'-(1-propynyl)tolan
No. 146: 4-[2-(trans-4-pentylcyclohexyl)ethyl]-4'-(1-butynyl)tolan
No. 147: 4-[2-(trans-4-pentylcyclohexyl)ethyl]-4'-(1-pentynyl)tolan
No. 148: 4-[2-(trans-4-pentylcyclohexyl)ethyl]-4'-(1-hexynyl)tolan
No. 149: 4-[2-(trans-4-pentylcyclohexyl)ethyl]-4'-(1-heptynyl)tolan
No. 150: 4-[2-(trans-4-pentylcyclohexyl)ethyl]-4'-(1-octynyl)tolan
No. 151: 4-[2-(trans-4-pentylcyclohexyl)ethyl]-4'-(1-nonynyl)tolan
No. 152: 4-[2-(trans-4-pentylcyclohexyl)ethyl]-4'-(1-decynyl)tolan
No. 153: 4-[2-(trans-4-hexylcyclohexyl)ethyl]-4'-(1-propynyl)tolan
No. 154: 4-[2-(trans-4-hexylcyclohexyl)ethyl]-4'-(1-butynyl)tolan
No. 155: 4-[2-(trans-4-hexylcyclohexyl)ethyl]-4'-(1-pentynyl)tolan
No. 156: 4-[2-(trans-4-hexylcyclohexyl)ethyl]-4'-(1-hexynyl)tolan
No. 157: 4-[2-(trans-4-hexylcyclohexyl)ethyl]-4'-(1-heptynyl)tolan
No. 158: 4-[2-(trans-4-hexylcyclohexyl)ethyl]-4'-(1-octynyl)tolan
No. 159: 4-[2-(trans-4-hexylcyclohexyl)ethyl]-4'-(1-nonynyl)tolan
No. 160: 4-[2-(trans-4-hexylcyclohexyl)ethyl]-4'-(1-decynyl)tolan
No. 161: 4-[2-(trans-4-heptylcyclohexyl)ethyl]-4'-(1-propynyl)tolan
No. 162: 4-[2-(trans-4-heptylcyclohexyl)ethyl]-4'-(1-butynyl)tolan
No. 163: 4-[2-(trans-4-heptylcyclohexyl)ethyl]-4'-(1-pentynyl)tolan
No. 164: 4-[2-(trans-4-heptylcyclohexyl)ethyl]-4'-(1-hexynyl)tolan
No. 165: 4-[2-(trans-4-heptylcyclohexyl)ethyl]-4'-(1-heptynyl)tolan
No. 166: 4-[2-(trans-4-heptylcyclohexyl)ethyl]-4'-(1-octynyl)tolan No. 167: 4-[2-(trans-4-heptylcyclohexyl)ethyl]-4'-(1-nonynyl)tolan
No. 168: 4-[2-(trans-4-heptylcyclohexyl)ethyl]-4'-(1-decynyl)tolan
No. 169: 4-[2-(trans-4-octylcyclohexyl)ethyl]-4'-(1-propynyl)tolan
No. 170: 4-[2-(trans-4-octylcyclohexyl)ethyl]-4'-(1-butynyl)tolan
No. 171: 4-[2-(trans-4-octylcyclohexyl)ethyl]-4'-(1-pentynyl)tolan
No. 172,: 4-[2-(trans-4-octylcyclohexyl)ethyl]-4'-(1-hexynyl)tolan
No. 173: 4-[2-(trans-4-octylcyclohexyl)ethyl]-4'-(1-heptynyl)tolan
No. 174: 4-[2-(trans-4-octylcyclohexyl)ethyl]-4'-(1-octynyl)tolan
No. 175: 4-[2-(trans-4-octylcyclohexyl)ethyl]-4'-(1-nonynyl)tolan
No. 176: 4-[2-(trans-4-octylcyclohexyl)ethyl]-4'-(1-decynyl)tolan
No. 177: 2-fluoro-4-[2-(trans-4-propylcyclohexyl)ethyl]-4'-(1-propynyl)tolan
No. 178: 2-fluoro-4-[2-(trans-4-propylcyclohexyl)ethyl]-4'-(1-butynyl)tolan
No. 179: 2-fluoro-4-[2-(trans-4-propylcyclohexyl)ethyl]-4'-(1-pentynyl)tolan
No. 180: 2-fluoro-4-[2-(trans-4-butylcyclohexyl)ethyl]-4'-(1-propynyl)tolan
No. 181: 2-fluoro-4-[2-(trans-4-butylcyclohexyl)ethyl]-440 -(1-butynyl)tolan
No. 182: 2-fluoro-4-[2-(trans-4-butylcyclohexyl)ethyl]-4'-(1-pentynyl)tolan
No. 183: 2-fluoro-4-[2-(trans-4-pentylcyclohexyl)ethyl]-4'-(1-propynyl)tolan
No. 184: 2-fluoro-4-[2-(trans-4-pentylcyclohexyl)ethyl]-4'-(1-butynyl)tolan
No. 185: 2-fluoro-4-[2-(trans-4-pentylcyclohexyl)ethyl]-4'-(1-pentynyl)tolan

EXAMPLE 4

Preparation of 4-(4-propylphenyl)-4'-(1-propynyl)tolan

4-Ethynyl-4'-propylbiphenyl (prepared according to the method disclosed in Japanese patent application laid-open No. Sho 58-110527/1983) (2.2 g, 0.01 mol) and 4-(1-propynyl)iodobenzene (2.4 g, 0.01 mol) were dissolved in diethylamine (20 ml), and then copper iodide (0.11 g, 0.15 mmol) and dichlorobistriphenylphosphinepalladium dichloride (0.21 g, 0.3 mmol) were added. The resulting mixture was subjected to reaction and purification operation in the same manner as in Example 1, to obtain the objective 4-(4-propylphenyl)-4'-(1-propynyl)tolan (compound No. 186) (1.7 g).

The following compounds are prepared in the same manner as above:
Compound No. 187: 4-(4-ethylphenyl)-4'-(1-propynyl)tolan
No. 188: 4-(4-ethylphenyl)-4'-(1-butynyl)tolan
No. 189: 4(4-ethylphenyl)-4'-(1-pentynyl)tolan
No. 190: 4(4-ethylphenyl)-4'-(1-hexynyl)tolan
No. 191: 4(4-propylphenyl)-4'-(1-butynyl)tolan
No. 192: 4-(4-propylphenyl)-4'-(1-pentynyl)tolan
No. 193: 4(4-propylphenyl)-4'-(1-hexynyl)tolan
No. 194: 4(4-butylphenyl)-4'-(1-propynyl)tolan
No. 195: 4(4-butylphenyl)-4'-(1-butynyl)tolan
No. 196: 4-(4-butylphenyl)-4'-(1-pentynyl)tolan
No. 197: 4(4-butylphenyl)-4'-(1-hexynyl)tolan
No. 198: 4(4-pentylphenyl)-4'-(1-propynyl)tolan
No. 199: 4-(4-pentylphenyl)-4'-(1-butynyl)tolan
No. 200: 4-(4-pentylphenyl)-4'-(1-pentynyl)tolan
No. 201: 4-(4-pentylphenyl)-4'-(1-hexynyl)tolan
No. 202: 4-(4-hexylphenyl)-4'-(1-propynyl)tolan
No. 203: 4-(4-hexylphenyl)-4'-(1-butynyl)tolan
No. 204: 4-(4-hexylphenyl)-4'-(1-pentynyl)tolan
No. 205: 4(4-hexylphenyl)-4'-(1-hexynyl)tolan
No. 206: 4(4-heptylphenyl)-4'-(1-propynyl)tolan
No. 207: 4(4-heptylphenyl)-4'-(1-butynyl)tolan
No. 208: 4(4-heptylphenyl)-4'-(1-pentynyl)tolan
No. 209: 4(4-heptylphenyl)-4'-(1-hexynyl)tolan
No. 210: 4(4-octylphenyl)-4'-(1-propynyl)tolan
No. 211: 4(4-octylphenyl)-4'-(1-butynyl)tolan
No. 212: 4(4-octylphenyl)-4'-(1-pentynyl)tolan
No. 213: 4(4-octylphenyl)-4'-(1-hexynyl)tolan
No. 214: 2-fluoro-4-(4-propylphenyl)-4'-(1-propynyl)tolan
No. 215: 2-fluoro-4-(4-propylphenyl)-4'-(1-butynyl)tolan
No. 216: 2-fluoro-4-(4-propylphenyl)-4'-(1-pentynyl)tolan
No. 217: 2-fluoro-4-(4-butylphenyl)-4'-(1-propynyl)tolan
No. 218: 2-fluoro-4-(4-butylphenyl)-4'-(1-butynyl)tolan
No. 219: 2-fluoro-4-(4-butylphenyl)-4'-(1-pentynyl)tolan
No. 220: 2-fluoro-4-(4-pentylphenyl)-4'-(1-propynyl)tolan
No. 221: 2-fluoro-4-(4-pentylphenyl)-4'-(1-butynyl)tolan
No. 222: 2-fluoro-4-(4-pentylphenyl)-4'-(1-pentynyl)tolan

EXAMPLE 5

Preparation of 4-(trans-4-propylcyclohexylcarbonyloxy)-4'-(1-propynyl)tolan

Trans-4-propylcyclohexanecarboxylic acid-p-ethylphenyl ester (which can be obtained by subjecting 4-hydroxyphenylacetylene obtained from 4-hydroxyacetophenone as a raw material and trans-4-propylcyclohexanecarboxylic acid to esterification reaction in a conventional manner) (2.7 g, 0.01 mol) and 4-(1-propynyl)iodobenzene (2.4 g, 0.01 mol) were dissolved in diethylamine (20 ml ), and then copper iodide (0.11 g, 0.15 mmol) and dichlorobistriphenylphosphinepalladium dichloride (0.21 g, 0.3 mmol) were added. The resulting mixture was subjected to reaction and purification operation in the same manner as in Example 1 to obtain the objective b 4-(trans-4-propylcyclohexylcarbonyloxy)-4'-(1-propynyl)tolan (compound No. 223) (1.3 g).

The following compounds are obtained in the same manner as above:
No. 224: 4-(trans-4-ethylcyclohexylcarbonyloxy)-4'-(1-propynyl)tolan
No. 225: 4-(trans-4-ethylcyclohexylcarbonyloxy)-4'-(1-butynyl)tolan
No. 226: 4-trans -4-ethylcyclohexylcarbonyloxy)-4'-(1-pentynyl)tolan
No. 227: 4-(trans-4-ethylcyclohexylcarbonyloxy)-4'-(1-hexynyl)tolan
No. 228: 4-(trans-4-propylcyclohexylcarbonyloxy)-4'-(1-butynyl)tolan
No. 229: 4-(trans-4-propylcyclohexylcarbonyloxy)-4'-(1-pentynyl)tolan No. 230: 4-(trans-4-propylcyclohexylcarbonyloxy)-4'-(1-hexynyl)tolan
No. 231: 4-(trans-4-butylcyclohexylcarbonyloxy)-4'-(1-propynyl)tolan
No. 232: 4-(trans-4-butylcyclohexylcarbonyloxy)-4'-(1-butynyl)tolan
No. 233: 4-(trans-4-butylcyclohexylcarbonyloxy)-4'-(1-pentynyl)tolan
No. 234: 4-(trans-4-butylcyclohexylcarbonyloxy)-4'-(1-hexynyl)tolan
No. 235: 4-(trans-4-pentylcyclohexylcarbonyloxy)-4'-(1-propynyl)tolan
No. 236: 4-(trans-4-pentylcyclohexylcarbonyloxy)-4'-(1-butynyl)tolan
No. 237: 4-(trans-4-pentylcyclohexylcarbonyloxy)-4'-(1-pentynyl)tolan
No. 238: 4-(trans-4-pentylcyclohexylcarbonyloxy)-4'-(1-hexynyl)tolan
No. 239: 4-(trans-4-hexylcyclohexylcarbonyloxy)-4'-(1-propynyl)tolan
No. 240: 4-(trans-4-hexylcyclohexylcarbonyloxy)-4'-(1-butynyl)tolan
No. 241: 4-(trans-4-hexylcyclohexylcarbonyloxy)-4'-(1-pentynyl)tolan
No. 242: 4-(trans-4-hexylcyclohexylcarbonyloxy)-4'-(1-hexynyl)tolan
No. 243: 4-(trans-4-heptylcyclohexylcarbonyloxy)-4'-(1-propynyl)tolan
No. 244: 4-(trans-4-heptylcyclohexylcarbonyloxy)-4'-(1-butynyl)tolan
No. 245: 4-(trans-4-heptylcyclohexylcarbonyloxy)-4'-(1-pentynyl)tolan
No. 246: 4-(trans-4-heptylcyclohexylcarbonyloxy)-4'-(1-hexynyl)tolan
No. 247: 4-(trans-4-octylcyclohexylcarbonyloxy)-4'-(1-propynyl)tolan
No. 248: 4-(trans-4-octylcyclohexylcarbonyloxy)-4'-(1-butynyl)tolan
No. 249: 4-(trans-4-octylcyclohexylcarbonyloxy)-4'-(1-pentynyl)tolan
No. 250: 4-(trans-4-octylcyclohexylcarbonyloxy)-4'-(1-hexynyl)tolan
No. 251: 2-fluoro-4-(trans-4-propylcyclohexylcarbonyloxy)-4'-(1-propynyl)tolan
No. 252: 2-fluoro-4-(trans-4-propylcyclohexylcarbonyloxy)-4'-(1-butynyl)tolan
No. 253: 2-fluoro-4-(trans-4-propylcyclohexylcarbonyloxy)-4'-(1-pentynyl)tolan
No. 254: 2-fluoro-4-(trans-4-butylcyclohexylcarbonyloxy)-4'-(1-propynyl)tolan
No. 255: 2-fluoro-4-(trans-4-butylcyclohexylcarbonyloxy)-4'-(1-butynyl)tolan
No. 256: 2-fluoro-4-(trans-4-butylcyclohexylcarbonyloxy)-4'-(1-pentynyl)tolan
No. 257: 2-fluoro-4-(trans-4-pentylcyclohexylcarbonyloxy)-4'-(1-propynyl)tolan
No. 258: 2-fluoro-4-(trans-4-pentylcyclohexylcarbonyloxy)-4'-(1-butynyl)tolan
No. 259: 2-fluoro-4-(trans-4-pentylcyclohexylcarbonyloxy)-4'-(1-pentynyl)tolan
No. 260: 4-(4-ethylbenzoyloxy)-4'-(1-propynyl)tolan
No. 261: 4-(4-ethylbenzoyloxy)-4'-(1-butynyl)tolan
No. 262: 4-(4-ethylbenzoyloxy)-4'-(1-pentynyl)tolan
No. 263: 4-(4-ethylbenzoyloxy)-4'-(1-hexynyl)tolan
No. 264: 4-(4-propylbenzoyloxy)-4'-(1-propynyl)tolan
No. 265: 4-(4-propylbenzoyloxy)-4'-(1-butynyl)
No.
No. 266: 4-(4-propylbenzoyloxy)-4'-(1-pentynyl)tolan
No. 267: 4-(4-propylbenzoyloxy)-4'-(1-hexynyl)tolan
No. 268: 4-(4-butylbenzoyloxy)-4'-(1-propynyl)tolan
No. 269: 4-(4-butylbenzoyloxy)-4'-(1-butynyl)tolan
No. 270: 4-(4-butylbenzoyloxy)-4'-(1-pentynyl)tolan
No. 271: 4-(4-butylbenzoyloxy)-4'-(1-hexynyl)tolan
No. 272: 4-(4-pentylbenzoyloxy)-4'-(1-propynyl)tolan
No. 273: 4-(4-pentylbenzoyloxy)-4'-(1-butynyl)tolan
No. 274: 4-(4-pentylbenzoyloxy)-4'-(1-pentynyl)tolan
No. 275: 4-(4-pentylbenzoyloxy)-4'-(1-hexynyl)tolan
No. 276: 4-(4-hexylbenzoyloxy)-4'-(1-propynyl)tolan
No. 277: 4-(4-hexylbenzoyloxy)-4'-(1-butynyl)tolan
No. 278: 4-(4-hexylbenzoyloxy)-4'-(1-pentynyl)tolan
No. 279: 4-(4-(4-hexylbenzoyloxy)-4'-(1-hexynyl)tolan
No. 280: 4-(4-heptylbenzoyloxy)-4'-(1-propynyl)tolan
No. 281: 4-(4-heptylbenzoyloxy)-4'-(1-butynyl)tolan
No. 282: 4-(4-heptylbenzoyloxy)-4'-(1-pentynyl)tolan
No. 283: 4-(4-heptylbenzoyloxy)-4'-(1-hexynyl)tolan
No. 284: 4-(4-octylbenzoyloxy)-4'-(1-propynyl)tolan
No. 285: 4-(4-octylbenzoyloxy)-4'-(1-butynyl)tolan
No. 286: 4-(4-octylbenzoyloxy)-4'-(1-pentynyl)tolan
No. 287: 4-(4-octylbenzoyloxy)-4'-(1-hexynyl)tolan
No. 288: 2-fluoro-4-(4-propylbenzoyloxy)-4'-(1-propynyl)tolan
No. 289: 2-fluoro-4-(4-propylbenzoyloxy)-4'-(1-butynyl)tolan
No. 290: 2-fluoro-4-(4-propylbenzoyloxy)-4'-(1-pentynyl)tolan
No. 291: 2-fluoro-4-(4-butylbenzoyloxy)-4'-(1-propynyl)tolan
No. 292: 2-fluoro-4-(4-butylbenzoyloxy)-4'-(1-butynyl)tolan
No. 293: 2-fluoro-4-(4-butylbenzoyloxy)-4'-(1-pentynyl)tolan
No. 294: 2-fluoro-4-(4-pentylbenzoyloxy)-4'-(1-propynyl)tolan
No. 295: 2-fluoro-4-(4-pentylbenzoyloxy)-4'-(1-butynyl)tolan
No. 296: 2-fluoro-4-(4-pentylbenzoyloxy)-4'-(1-pentynyl)tolan

EXAMPLE 6

Preparation of 4-methoxy-4'-(1-propynyl)tolan

4-Methoxyphenyl acetylene (2.65 g, 0.02 mol) and 4-(1-propynyl)iodobenzene (5.0 g, 0.02 mol) were dissolved in diethylamine (20 ml), and then added copper iodide (0.06 g) and dichlorobistriphenylphosphinepalladium dichloride (0.21 g) were added. The resulting mixture was subjected to reaction and purification operations in the same manners as in Example 1, to obtain the objective 4-methoxy-4'-(1-propynyl)tolan (No. 297) (1.35 g).

The following compounds are prepared in the same manner as above:
No. 298: 4-methoxy-4'-(1-butynyl)tolan
No. 299: 4-methoxy-4'-(1-pentynyl)tolan
No. 300: 4-methoxy-4'-(1-hexynyl)tolan
No. 301: 4-methoxy-4'-(1-heptynyl)tolan
No. 302: 4-methoxy-4'-(1-octynyl)tolan
No. 303: 4-methoxy-4'-(1-nonynyl)tolan
No. 304: 4-methoxy-4'-(1-decynyl)tolan
No. 305: 4-ethoxy-4'-(1-propynyl)tolan
No. 306: 4-ethoxy-4'-(1-butynyl)tolan
No. 307: 4-ethoxy-4'-(1-pentynyl)tolan
No. 308: 4-ethoxy-4'-(1-hexynyl)tolan
No. 309: 4-ethoxy-4'-(1-heptynyl)tolan
No. 310: 4-ethoxy-4'-(1-octynyl)tolan
No. 311: 4-ethoxy-4'-(1-nonynyl)tolan No. 312: 4-ethoxy-4'-(1-decynyl)tolan
No. 313: 4-propoxy-4'-(1-butynyl)tolan
No. 314: 4-propoxy-4'-(1-pentynyl)tolan
No. 315: 4-propoxy-4'-(1-hexynyl)tolan
No. 316: 4-propoxy-4'-(1-heptynyl)tolan
No. 317: 4-propoxy-4'-(1-octynyl)tolan
No. 318: 4-propoxy-4'-(1-nonynyl)tolan
No. 319: 4-propoxy-4'-(1-decynyl)tolan
No. 320: 4-butoxy-4'-(1-propynyl)tolan
No. 321: 4-butoxy-4'-(1-butynyl)tolan
No. 322: 4-butoxy-4'-(1-pentynyl)tolan
No. 323: 4-butoxy-4'-(1-hexynyl)tolan
No. 324: 4-butoxy-4'-(1-heptynyl)tolan
No. 325: 4-butoxy-4'-(1-octynyl)tolan
No. 326: 4-butoxy-4'-(1-nonynyl)tolan
No. 327: 4-butoxy-4'-(1-decynyl)tolan
No. 328: 4-pentyloxy-4'-(1-propynyl)tolan
No. 329: 4-pentyloxy-4'-(1-butynyl)tolan
No. 330: 4-pentyloxy-4'-(1-pentynyl)tolan
No. 331: 4-pentyloxy-4'-(1-hexynyl)tolan
No. 332: 4-pentyloxy-4'-(1-heptynyl)tolan
No. 333: 4-pentyloxy-4'-(1-octynyl)tolan
No. 334: 4-pentyloxy-4'-(1-nonynyl)tolan
No. 335: 4-pentyloxy-4'-(1-decynyl)tolan
No. 336: 4-hexyloxy-4'-(1-propynyl)tolan
No. 337: 4-hexyloxy-4'-(1-butynyl)tolan
No. 338: 4-hexyloxy-4'-(1-pentynyl)tolan
No. 339: 4-hexyloxy-4'-(1-hexynyl)tolan
No. 340: 4-hexyloxy-4'-(1-heptynyl)tolan
No. 342: 4-hexyloxy-4'-(1-nonynyl)tolan
No. 343: 4-hexyloxy-4'-(1-decynyl)tolan
No. 344: 4-heptyloxy-4'-(1-propynyl)tolan
No. 345: 4-heptyloxy-4'-(1-butynyl)tolan
No. 346: 4-heptyloxy-4'-(1-pentynyl)tolan
No. 347: 4-heptyloxy-4'-(1-hexynyl)tolan
No. 348: 4-heptyloxy-4'-(1-heptynyl)tolan
No. 349: 4-heptyloxy-4'-(1-octynyl)tolan
No. 350: 4-heptyloxy-4'-(1-nonynyl)tolan
No. 351: 4-heptyloxy-4'-(1-decynyl)tolan
No. 352: 4-octyloxy-4'-(1-propynyl)tolan
No. 353: 4-octyloxy-4'-(1-butynyl)tolan
No. 354: 4-octyloxy-4'-(1-pentynyl)tolan
No. 355: 4-octyloxy-4'-(1-hexynyl)tolan
No. 356: 4-octyloxy-4'-(1-heptyl)tolan
No. 357: 4-octyloxy-4'-(1-octynyl)tolan
No. 358: 4-octyloxy-4'-(1-nonynyl)tolan
No. 359: 4-octyloxy-4'-(1-decynyl)tolan

EXAMPLE 7

(Use Example 1)

A liquid crystal composition A consisting of

A {
C₃H₇—⬡—COO—⬢—OC₄H₉    27.6 wt. parts
C₄H₉—⬡—COO—⬢—OC₂H₅    20.7 wt. parts
C₅H₁₁—⬡—COO—⬢—OCH₃    20.7 wt. parts
C₃H₇—⬡—COO—⬢—OC₂H₅    17.2 wt. parts
C₅H₁₁—⬡—COO—⬢—OC₂H₅   13.8 wt. parts
} has an NI point of 72.4° C., a viscosity at 20° C. $\eta_{20}$ of 20.1 cp and a Δn of 0.087. A liquid crystal composition B obtained by adding 15 parts by weight of 4-propyl-4'-(1-propynyl)tolan shown in Example 1 of the present invention to 85 parts by weight of the composition A had an NI point of 72.0° C. and a $\eta_{20}$ of 20.0 cp, that is, these values were almost unchanged, but the Δn value rose to 0.126.

EXAMPLE 8

(Use Example 2)

A liquid crystal composition C consisting of

C {
C₃H₇—⬡—⬢—CN    30 wt. parts
C₅H₁₁—⬡—⬢—CN   40 wt. parts
C₉H₁₅—⬡—⬢—CN   30 wt. parts
} has an NI point of 52.3° C., a viscosity at 20° C. $\eta_{20}$ of 21.7 cp and a Δn of 0.119. A liquid crystal composition D obtained by adding 15 parts by weight of 4-propyl-4'-(1-pentynyl)tolan (compound
No. 11 of the present invention shown above) to 85 parts by weight of the liquid crystal composition C had an NI point of 49.6° C. (that is, slightly lowered) and a $\eta_{20}$ of 21.7 (that is, unchanged), but the Δn rose to 0.137.

As seen from these Use examples, the compound of the present invention has a very large effect of making the reduction in the NI point of the liquid crystal composition obtained by using the compound as small as possible, without raising the viscosity, but raising the optical anisotropy value Δn.

According to the present invention, it is possible to obtain a liquid crystal compound and a liquid crystal composition having a large optical anisotropy Δn value and yet a low viscosity, and besides, having well-balanced characteristics as liquid crystal materials for display.

What we claim is:

1. A substituted-4'-(1-alkynyl)tolan compound expressed by the formula (I):

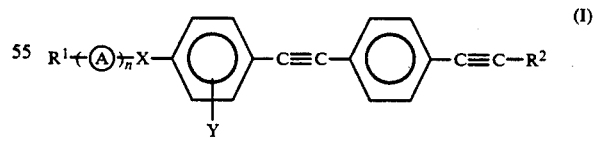

(I)

wherein
R¹ represents an alkyl or alkoxy group each of 1 to 8 carbon atoms;
R² represents an alkyl group of 1 to 8 carbon atoms;
—Ⓐ— represent unsubstituted 1,4-phenylene, 1,4-phenylene having one or two substituents selected from the group consisting of fluorine, chlorine, bromine and cyano, or 1,4-cyclohexylene;
X represents —CH₂CH₂— or a single bond;

n represents 0 or 1, and when n represents O, X represents a single bond; and

Y represents hydrogen or fluorine.

2. A tolan compound according to claim 1, wherein n represents 0 and X represents a single bond in the formula (I).

3. A tolan compound according to claim 1, wherein n represents 1, —(A)— represents

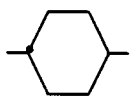

and X represents a single bond in the formula (I).

4. A tolan compound according to claim 1, wherein n represents 1, —(A)— represents

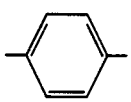

and X represents a single bond in the formula (I).

5. A tolan compound according to claim 1, wherein n represents 1, (A)— represents

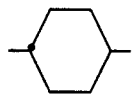

and X represents —CH$_2$—CH$_2$— in the formula (I).

6. A liquid crystal composition comprising at least two components at least one of which is a tolan compound as set forth in claim 1.

7. A liquid crystal element, wherein a nematic liquid crystal having a positive dielectric anisotropy value and having a rotatory polarization substance added thereto, is sealed between a pair of upper and lower electrode substrates opposed to each other; liquid crystal molecules form a 160°-270°-twisted, helical structure in the thickness direction thereof; the polarization axis of polarizing plates provided for placing the helical structure therebetween deviates within a range of 20° to 70° against the direction of liquid crystal molecule arrangement in the electrode substrates; the product of the thickness of the liquid crystal layer (d) by the optical anisotropy value of the liquid crystal layer ($\Delta$n), that is, $\Delta$n×d, is in the range of 0.7 to 1.2 μm; and a liquid crystal composition containing 0.1 to 40% by weight based on the composition, of at least one tolan compound as set forth in claim 10 is contained in said liquid crystal element.

* * * * *

UNITED STATES PATENT AND TRADEMARK OFFICE
CERTIFICATE OF CORRECTION

PATENT NO. : 5,154,851
DATED : October 13, 1992
INVENTOR(S) : Yasuyuki Goto, et. al.

It is certified that error appears in the above-identified patent and that said Letters Patent is hereby corrected as shown below:

Column 8, line 57, delete "b" before "81.0°".

Column 10, line 27, delete " < ".

Column 13, line 30, change "440" to --4'--.

Column 15, line 66, change "(1-butynyl)" to --(1-butynyl)tolan--;
   line 67, delete "No.".

Claim 1, line 3 from the bottom (column 19, line 1), change "0," before "X" to --0,-- (zero).

Column 20, line 2 from the bottom, change "10" to --1--.

Signed and Sealed this

Nineteenth Day of October, 1993

Attest:

BRUCE LEHMAN

Attesting Officer    Commissioner of Patents and Trademarks